United States Patent [19]

Hooper et al.

[11] Patent Number: 4,469,848

[45] Date of Patent: Sep. 4, 1984

[54] DEODORANT PRODUCT FOR SURFACE TREATMENT

[75] Inventors: David C. Hooper, Ashford; George A. Johnson, Wirral; Donald Peter, Wirral; George K. Rennie, Wirral, all of England

[73] Assignee: Lever Brothers Company, New York, N.Y.

[21] Appl. No.: 353,313

[22] Filed: Feb. 12, 1982

Related U.S. Application Data

[62] Division of Ser. No. 38,981, May 14, 1979, Pat. No. 4,347,153.

[30] Foreign Application Priority Data

May 16, 1978 [GB] United Kingdom ............... 19844/78

[51] Int. Cl.$^3$ .......................... C11D 3/50; C11D 7/22
[52] U.S. Cl. ........................................ 252/106; 106/3; 106/10; 252/174.11; 252/174.23; 252/174.25; 252/164; 252/522 R; 252/DIG. 10; 252/2; 252/3; 424/76; 424/78
[58] Field of Search ................. 106/3, 10; 252/174.11, 252/174.23, 174.25, 164, 522, DIG. 10, 106, DIG. 2, DIG. 3; 424/76, 78

[56] References Cited

U.S. PATENT DOCUMENTS

| | | | |
|---|---|---|---|
| 2,875,131 | 2/1959 | Carpenter et al. | 252/522 X |
| 3,413,252 | 11/1968 | Lima | 106/3 X |
| 3,669,892 | 6/1972 | Abler et al. | 252/90 |
| 3,959,530 | 5/1976 | Kaliardos | 427/341 |
| 4,134,838 | 1/1979 | Hooper et al. | 252/8.8 |

FOREIGN PATENT DOCUMENTS

| | | |
|---|---|---|
| 7604601 | 8/1977 | Brazil . |
| 1519414 | 6/1972 | Fed. Rep. of Germany . |
| 46303 | 4/1978 | Japan . |

OTHER PUBLICATIONS

Bennett, H., *The Chemical Formulary*, Chemical Publishing Co., N.Y., vol. XV, p. 257.

*Primary Examiner*—P. E. Willis, Jr.
*Attorney, Agent, or Firm*—James J. Farrell

[57] ABSTRACT

A deodorant product comprises a deodorant composition and a polishing agent, chosen from waxes, film-forming polymers or mixtures thereof, the deodorant composition having a deodorant value of from 0.50 to 3.5 as measured by the Deodorant Value Test.

17 Claims, No Drawings

DEODORANT PRODUCT FOR SURFACE TREATMENT

This is a divisional application of Ser. No. 038,981 filed May 14, 1979 now U.S. Pat. No. 4,347,153.

The invention relates to deodorant products suitable for application to surfaces other than human skin, in domestic, commercial, industrial and agricultural situations where malodour presents a problem.

BACKGROUND TO THE INVENTION

It has long been realised that malodour, whether originating from the human body or from other sources, particularly in the domestic, commercial, industrial and agricultural environments can constitute an unpleasant experience and that benefit could be obtained by preventing the development of malodours or by masking or otherwise obliterating malodours where they already exist.

As a means for solving this problem it is recognised that perfumes have been used as odour maskants since ancient times and that perfumes have for this reason been incorporated into all manner of consumer products for use in the human environment.

It is, however, recognised that the use of perfumes in this manner has its limitations, in that the duration of effectiveness can be relatively short-lived, or that offensive malodours are only partially masked.

SUMMARY OF THE INVENTION

It has now been discovered that certain combinations of materials, some of which can be perfumery materials, and hereinafter referred to as "deodorant compositions", when incorporated into products for use in the human environment can provide a more effective means for preventing malodour development or for reducing the perception of malodours which are already present. Although the products of the invention may be fragrant, it is apparent that their effectiveness as deodorants is not solely due to odour masking, since in many instances there is no detectable residual fragrance of the composition remaining after its application or deployment. Accordingly, the use of deodorant compositions in such products represents a new operative principle.

In the course of attempts to characterise this new principle, many hundreds of materials have been screened and hundreds of formulations made by blending these materials have been examined.

DEFINITION OF THE INVENTION

In its widest aspect, the invention provides a deodorant product for application to surfaces other than human skin, which product comprises a deodorising amount of a deodorant composition and a carrier for the composition chosen from abrasive materials, bleaching agents, waxes, film-forming polymers, or mixtures thereof, the deodorant composition having a deodorant value of from 0.50 to 3.5 as measured by the Deodorant Value test.

The invention also provides a process for preparing a deodorant product for application to surfaces other than human skin, which process comprises mixing a deodorant composition with a carrier for the composition chosen from abrasive materials, bleaching agents, waxes, film-forming polymers, or mixtures thereof, to provide a deodorant product, the deodorant composition having a deodorant value of from 0.50 to 3.5 as measured by the Deodorant Value test.

The invention furthermore provides a method for suppressing malodour which comprises deploying an effective amount of a deodorant product comprising a deodorant composition and a carrier for the composition as hereindefined, the deodorant composition having a deodorant value of from 0.50 to 3.5 as measured by the Deodorant Value test.

THE DEODORANT VALUE TEST

In this test the deodorant value of a deodorant composition is measured by assessing its effectiveness, when contained in a standard soap bar at a standard concentration, in reducing body malodour when the standard soap bar is used to wash the axillae (armpits) of a panel of human subjects.

The choice of a soap base is not critical to the performance of the test but as illustrative of the conduct of the test in this respect the procedure followed in the preparation of the base is included in the description of the test.

Standard soap bars are prepared as follows, all amounts given being by weight.

As soap base there is used a neutral wet sodium soap containing 63% of total fatty matter of which 82% is tallow fatty acid and 18% is coconut oil fatty acid. To a homogeneous mixture of 9000 parts of this soap base and 340 parts of free coconut oil fatty acid at 80° C. are added with mixing, 9.4 parts of a 20% aqueous solution of tetrasodium ethylenediamine tetraacetate, 2.2 parts of a 60% aqueous solution of 1-hydroxyethane-1,1-diphosphonic acid and 7.2 parts of butylated hydroxy toluene (BHT) antioxidant dissolved in a little methylated spirits and the temperature of the mass is raised to 140° C. under superatmospheric pressure. The mass is then sprayed at about 30 mm of mercury, to produce a dried soap composition which is collected and extruded at 30° C. as noodles of about 12% moisture content.

9,770 parts of the soap noodles thus obtained are mixed at ambient temperature with 150 parts of the deodorant composition to be tested, together with 30 parts of a titanium dioxide opacifier and 50 parts of a colourant suspension. The resulting mixture is milled and stamped into tablets. The deodorant composition to be tested is therefore present at the standard level of 1.5%.

Control soap bars are prepared in a similar manner except that the deodorant composition is omitted. In other respects, the control bar should only contain those additives conventionally present in personal washing products and for the purpose in the amount conventionally used in the art. For example, it is permissible as indicated in the foregoing description to include antioxidants in the control bar, but these should be present only in the amount required to stabilise the soap base.

The test is conducted as follows:

A team of 3 Caucasian female assessors of age within the range of from 20 to 40 years is selected for olfactory evaluation on the basis that each is able to rank correctly the odour levels of the series of aqueous isovaleric acid solutions listed in Table 1 below, and each is able to detect the reduction in body odour following application to the axillae of human subjects of soap containing 2% germicides, according to the procedure described in Whitehouse and Carter, Proc. Scientific Section of the Toilet Goods Association, 48, 31, (1967).

A panel of 50 human subjects for use in the test is assembled from Caucasian male subjects of age within the range of from 20 to 55 years. By screening, subjects are chosen who develop axilliary body malodour that is not unusually strong and who do not develop a stronger body malodour in one axilla compared with the other. Subjects who develop unusually strong body malodour, for example due to a diet including curry or garlic, are not selected for the panel.

For two weeks before the start of a test, the panel subjects are assigned a non-deodorant soap bar exclusively for use when bathing, and are denied the use of any type of deodorant or antiperspirant. At the end of this period, the 50 subjects are randomly divided into two groups of 25. The control soap bars are then applied to the left axillae of the first group and the right axillae of the second, and the test soap bars are applied to the right axillae of the first group and the left axillae of the second.

The soap bars are applied by a technician using a standard technique in which a wet flannel is soaped with the soap bar for 15 seconds, the axilla is washed with the soaped flannel for 30 seconds, then wiped with a water rinsed flannel and dried with a clean towel. Each subject then puts on a freshly laundered shirt, and 5 hours after application the odour intensity of each subject is assessed, the left axilla of each subject being assessed before the right. The application and assessment are carried out on each of four successive days.

The odour intensity is evaluated by all three assessors who, operating without knowledge of the soap bars used for each subject or the result of evaluation of their fellow-assessors, sniff each axilla and assign a score corresponding to the strength of the odour on a scale from 0 to 5, while 0 corresponding to no odour and 5 representing very strong odour. Before evaluation each subject stands with his arms against his side: he then raises one arm straight overhead, flattening the axilla vault and making it possible for the assessor's nose to be brought close to the skin, the assessor makes an evaluation and the procedure is repeated with the other axilla.

Standard aqueous solutions of isovaleric acid which correspond to each of the scores 1,2,3,4 and 5 are provided for reference to assist the assessors in the evaluation. These are shown in Table 1 below.

TABLE 1

| Score | Odour Level | Concentrations of aqueous solution of isovaleric acid (ml/l) |
|---|---|---|
| 0 | No odour | 0 |
| 1 | Slight | 0.013 |
| 2 | Definite | 0.053 |
| 3 | Moderate | 0.22 |
| 4 | Strong | 0.87 |
| 5 | Very strong | 3.57 |

The scores recorded by each assessor for each soap bar are averaged and the average score of the test soap bars deducted from the average score of the control soap bars to give the deodorant value of the deodorant composition present in the test soap bars.

As a check that the selection of panel subjects is satisfactory for operation of the test, the average score with the control soap bars should be between 2.5 and 3.5.

Although the invention in its widest aspect provides deodorant products comprising deodorant compositions having a deodorant value of from 0.50 to 3.5, preferred deodorant products are those comprising deodorant compositions which have a deodorant value of at least 0.60, or 0.8, or 1.0, or 1.2, or 1.5, the higher the minimum value, the more effective is the product as a deodorant product as recorded by the assessors in the deodorant value test.

1. THE DEODORANT COMPOSITION

The characterisation of the deodorant composition of the invention presents difficulties, since it cannot be defined solely in terms of materials of specified structure and combinations in specified proportions. Nevertheless, procedures have been discovered that enable the essential materials of the deodorant compositions to be identified by tests.

The essential materials required for the formulation of deodorant compositions are those having a lipoxidase-inhibiting capacity of at least 50% or those having a Raoult variance ratio of at least 1.1, as determined by the following tests, which are designated the lipoxidase and morpholine tests respectively.

THE LIPOXIDASE TEST

In this test the capacity of a material to inhibit the oxidation of linoleic acid by lipoxidase (EC1.13.1.13) to form a hydroperoxide is measured.

Aqueous 0.2M sodium borate solution (pH 9.0) is used as buffer solution.

A control substrate solution is prepared by dissolving linoleic acid (2.0 ml) in absolute ethanol (60 ml), diluting with distilled water to 100 ml and then adding borate buffer (100 ml) and absolute ethanol (300 ml).

A test substrate solution is prepared in the same way as the control substrate solution except that for the absolute ethanol (300 ml) is substituted the same volume of a 0.5% by weight solution in ethanol of the material to be tested.

A solution of the enzyme lipoxidase in the borate buffer and having an activity within the range of from 15,000 to 40,000 units per ml is prepared.

The activity of the lipoxidase in catalysing the oxidation of linoleic acid is first assayed spectrophotometrically using the control. An automatic continuously recording spectrophotometer is used and the increase in extinction at 234 nm (the peak of hydroperoxide) is measured to follow the course of oxidation, the enzyme concentration used being such that it gives an increase in optical density ($\Delta$OD) at 234 nm within the range of from 0.6 to 1.0 units per minute. The following ingredients are placed in two 3 ml cuvettes:

|  | Control (ml) | Blank (ml) |
|---|---|---|
| Control substrate solution | 0.10 | 0.10 |
| Absolute ethanol | 0.10 | 0.10 |
| Borate buffer | 2.75 | 2.80 |
| Lipoxidase solution | 0.05 | — |

The lipoxidase solution is added to the control cuvette last and the reaction immediately followed spectrophotometrically for about 3 minutes, with recording of the increase in optical density at 234 nm as a curve on a graph.

The capacity of a material to inhibit the oxidation is then measured using a test sample containing enzyme, substrate and a deodorant material. The following ingredients are placed in two 3 ml cuvettes.

|  | Test Sample (ml) | Blank (ml) |
|---|---|---|
| Test substrate solution | 0.10 | 0.10 |
| Absolute ethanol | 0.10 | 0.10 |
| Borate buffer | 2.75 | 2.80 |
| Lipoxidase solution | 0.05 | — |

The lipoxidase solution is added to the test sample cuvette last and the course of the reaction immediately followed as before.

The lipoxidase-inhibiting capacity of the material is then calculated from the formula $100(S_1-S_2)/S_1$, where $S_1$ is the slope of the curve obtained with the control and $S_2$ is the slope of the curve obtained with the test sample, and thus expressed as % inhibition. A material that gives at least 50% inhibition in the test is hereafter referred to as having a lipoxidase-inhibiting capacity of at least 50%.

THE MORPHOLINE TEST

In this test the capacity of a material to depress the partial vapour pressure of morpholine more than that required by Raoult's Law is measured. Substances that undergo chemical reaction with morpholine, for example aldehydes, are to be regarded as excluded from the test.

Into a sample bottle of capacity 20 ml is introduced morpholine (1 g) the bottle fitted with a serum cap and then maintained at 37° C. for 30 minutes for equilibrium to be reached. The gas in the headspace of the bottle is analysed by piercing the serum cap with a capillary needle through which nitrogen at 37° C. is passed to increase the pressure in the bottle by a standard amount and then allowing the excess pressure to inject a sample from the headspace into gas chromatograph apparatus, which analyses it and provides a chromatographic trace curve with a peak due to morpholine, the area under which is proportional to the amount of morpholine in the sample.

The procedure is repeated under exactly the same conditions using instead of morpholine alone, morpholine (0.25 g) and the material to be tested (1 g); and also using the material (1 g) without the morpholine to check whether it gives an interference with the morpholine peak (which is unusual).

The procedure is repeated until reproducible results are obtained. The areas under the morpholine peaks are measured and any necessary correction due to interference by the material is made.

A suitable apparatus for carrying out the above procedure is a Perkin-Elmer Automatic GC Multifract F40 for Head Space Analysis. Further details of this method are described by Kolb in "CZ-Chemie-Technik", Vol 1, No 2, 87-91 (1972) and by Jentzsch et al in "Z. Anal. Chem." 236, 96-118 (1968).

The measured areas representing the morpholine concentration are proportional to the partial vapour pressure of the morpholine in the bottle headspace. If A is the area under the morpholine peak when only morpholine is tested and A' is the area due to morpholine when a material is present, the relative lowering of partial vapour pressure of morpholine by the material is given by $1-A'/A$.

According to Raoult's Law, if at a given temperature the partial vapour pressure of morpholine in equlibrium with air above liquid morpholine is p, the partial vapour pressure p' exerted by morpholine in a homogeneous liquid mixture of morpholine and material at the same temperature is $pM/(M+PC)$, where M and PC are the molar concentrations of morpholine and material. Hence, according to Raoult's Law the relative lowering of morpholine partial vapour pressure $(p-p')/p$, is given by $1-M/(M+PC)$, which under the circumstances of the test is $87/(87+m/4)$, where m is the molecular weight of the perfume material.

The extent to which the behaviour of the mixture departs from Raoult's Law is give by the ratio $$\frac{1 - A'/A}{87/(87 + m/4)}$$

The above ratio, which will be referred to as the Raoult variance ratio, is calculated from the test results. Where a material is a mixture of compounds, a calculated or experimentally determined average molecular weight is used for m. A material that depresses the partial vapour pressure of morpholine by at least 10% more than that required by Raoult's Law is one in which the Raoult variance ratio is at least 1.1.

A large number of materials which satisfy one or both tests is described later in this specification and these are hereafter referred to as "components", in contrast to other materials which fail both tests which are referred to as "ingredients".

Before defining the more detailed aspects of the invention so far as it relates to deodorant compositions, it is necessary to clarify some of the terms that will be employed.

A composition is a blend of organic compounds. For the purposes of this specification it is necessary to identify the "components" in the composition. This is done by first describing the composition in terms of four categories. These categories are given below. Examples of components in each category are provided.

(1) Single chemical compounds whether natural or synthetic, e.g. coumarin (natural or synthetic), iso-eugenol, benzyl salicylate. The majority of components are in this category.

(2) Synthetic reaction products (products of reaction), mixtures of isomers an possibly homologues, e.g. α-iso-methyl ionone.

(3) Natural oils, gums and resins, and their extracts, e.g. patchouli oil, geranium oil, clove leaf oil, benzoin resinoid.

(4) Synthetic analogues of category 3. This category includes materials that are not strict analogues of natural oils, gums and resins but are materials that result from attempts to copy or improve upon materials of category 3, e.g. Bergamot AB 430, Geranium AB 76, Pomeransol AB 314.

Components of Categories (3) and (4) although often uncharacterised chemically are available commercially.

Where a material is supplied or used conventionally for convenience as a mixture, e.g. p-t-Amylcyclohexanone diluted with diethyl phthalate, for the purposes of this specification two components are present, so that use of 5% of a blend of 1 part of this ketone and 9 parts of diethyl phthalate is represented as 0.5% of the ketone and 4.5% of diethyl phthalate.

It has been found advantageous in formulating the most effective deodorant composition for incorporation into the deodorant product of the invention to use components that, well as satisfying the lipoxidase or morpholine tests, satisfy further conditions. These conditions are:

(i) there must be at least five components present,
(ii) each of these components must be selected from at least four different chemical classes (to be defined below),
(iii) a component from each of classes 1,2 and 4 must be present,
(iv) at least 45%, preferably at least 50 and most preferably from 60 to 100%, by weight of the deodorant composition must comprise components,
(v) a component is not considered to contribute to the efficacy of the deodorant composition if it is present in the deodorant composition at a concentration of less than 0.5% by weight, and
(vi) a class is not considered to contribute to the efficacy of the deodorant composition if it is present in the deodorant composition at a concentration of less than 0.5% by weight.

Therefore, according to a preferred embodiment of the invention, there is provided a deodorant product as herein defined in which the deodorant composition consists essentially of from about 45 to 100% by weight of at least five components and from 0 to about 55% by weight of ingredients, each of the components being selected from components having a lipoxidase inhibiting capacity of at least 50% and components having a Raoult variance ratio of at least 1.1, the components and ingredients being so chosen that the deodorant value of the deodorant composition is within the range 0.50 to 3.5.

Each component should be allocated to one of six classes. These classes are:
Class 1—Phenolic substances;
2—Essential oils, extracts, resins, "synthetic" oils (denoted by "AB");
3—Aldehydes and ketones;
4—Polycyclic compounds;
5—Esters;
6—Alcohols.

In attributing a component to a class, the following rules are to be observed. Where the component could be assigned to more than one class, the component is allocated to the class occurring first in the order given above: for example clove oil, which is phenolic in character, is placed in Class 1 although it otherwise might have been allocated to Class 2. Similarly, 2-n-heptyl cyclopentanone which is a polycyclic ketone is attributed to Class 3 instead of Class 4.

The following are examples of deodorant components that either have a lipoxidase inhibiting capacity (LIC) of at least 50% or have a Raoult variance ratio (RVR) of at least 1.1. Their class, molecular weight (m), LIC and RVR as determined by the tests already described herein are also listed.

The nomenclature adopted for the components listed below and for the ingredients which appear in the deodorant formulations of the Examples is, so far as is possible, that employed by Steffen Arctander in "Perfume and Flavour Chemicals (Aroma Chemicals)" Volumes I and II (1969) and the "Perfume & Flavour Materials of Natural Origin" (1960) by the same author. Where a component or other ingredient is not described by Arctander, then either the chemical name is given or, where this is not known (such as is the case with perfumery house specialities), then the supplier's identity can be established by reference to the appendix which appears at the end of the specification.

|  | LIC | RVR | m |
|---|---|---|---|
| Class 1 - Phenolic Substances | | | |
| iso-Amyl salicylate | 95 | 1.24 | 208 |
| Benzyl salicylate | 0 | 1.58 | 228 |
| Carvacrol | 32 | 1.43 | 150 |
| Clove leaf oil | 79 | 1.43 | 164 |
| Ethyl vanillin | 100 | 1.43 | 152 |
| iso-Eugenol | 100 | 1.48 | 164 |
| LRG 201 | 100 | 1.21 | 196 |
| Mousse de chene Yugo | 98 | 1.29 | 182 |
| Pimento leaf oil | 100 | — | 165 |
| Thyme oil red | 55 | 1.37 | 150 |
| Class 2 - Essential oils, extracts, resins, "synthetic" oils, (denoted by "AB") | | | |
| Benzoin Siam resinoid | 87 | — | — |
| Bergamot AB 37 | 58 | 0.97 | 175 |
| Bergamot AB 430 | 58 | 0.97 | 175 |
| Geranium AB 76 | 26 | 1.29 | 154 |
| Geranium oil | 26 | 1.29 | 154 |
| Opoponax resinoid | 96 | 1.33 | 150 |
| Patchouli oil | 76 | 1.25 | 140 |
| Petitgrain oil | 34 | 1.27 | 175 |
| Pomeransol AB 314 | 100 | — | — |
| Class 3 - Aldehydes and Ketones | | | |
| 6-Acetyl-1,1,3,4,4,6-hexamethyl-tetrahydronaphthalene | 100 | 1.03 | 258 |
| p-t-Amyl cyclohexanone | 50 | 1.10 | 182 |
| p-t-Butyl-α-methyl hydrocinnamic aldehyde | 74 | — | 204 |
| 2-n-heptylcyclopentanone | 56 | 1.05 | 182 |
| α-iso-Methyl ionone | 100 | 1.13 | 206 |
| β-Methyl naphthyl ketone | 100 | 0.96 | 170 |
| Class 4 - Polycyclic Compounds | | | |
| Coumarin | 58 | 1.22 | 146 |
| 1,3,4,6,7,8-Hexahydro-4,6,6,7,8,8-hexamethyl cyclopenta-α-2-benzopyran | 100 | — | 240 |
| 3a-Methyl-dodecahydro-6,6,9a-trimethylnaphtho(2,1-b)furan | 58 | 1.30 | 230 |
| β-Naphthyl methyl ether | 100 | — | 158 |
| Class 5 - Esters | | | |
| o-t-Butylcyclohexyl acetate | 52 | 1.08 | 198 |
| p-t-Butylcyclohexyl acetate | 54 | 0.98 | 198 |
| Diethyl phthalate | 79 | 1.20 | 222 |
| Nonanediol-1,3-diacetate | 33 | 1.17 | 244 |
| Nonanolide-1:4 | 92 | 0.87 | 156 |
| i-Nonyl acetate | 50 | 0.83 | 186 |
| i-Nonyl formate | 19 | 1.49 | 172 |
| Class 6 - Alcohols | | | |
| Dimyrcetol | 16 | 1.22 | 156 |
| Phenylether alcohol | 22 | 1.24 | 122 |
| Tetrahydromuguol | 24 | 1.23 | 158 |

It has been shown that for best results, a certain minimum average concentration of components should be present. This minimum concentration is a function of the number of classes present—the more classes present, the lower the minimum concentration. The minimum average concentration in the various situations that can apply is shown in the Table below:

| Number of classes represented in deodorant composition | Average concentration of components | |
|---|---|---|
| | minimum not less than (%) | preferably not less than (%) |
| 4 | 5 | 6 |
| 5 | 4.5 | 5.5 |
| 6 | 4.5 | 5 |

Also, it is preferred that at least 1% of each of four classes is present in the deodorant composition, but individual components which are present at a concentration of less than 0.5% are eliminated from this calculation, as is the class into which they fall if there is present no component at a concentration of at least 0.5% which falls within that class.

More specifically, the invention also provides a deodorant product as herein defined wherein the amount of deodorant components in the deodorant composition present in the classes 1,2 and 4 as herein defined is at least 1%, most preferably at least 3% by weight of the deodorant composition for each class, and the amount of components present in each of at least two other classes is at least 1% by weight of the composition, provided also that any component that is present in the deodorant composition at a concentration of less than a threshold value of 0.5% by weight is eliminated from the calculation of the amounts of components in each class.

Although at least four different classes of components should preferably be represented in the deodorant composition, superior compositions can be obtained if more than four classes are represented. Accordingly five or six classes can be represented in the deodorant composition.

It has been shown by the preparation, examination and testing of many hundreds of deodorant compositions that the best results are obtained by keeping within the aforementioned rules when selecting types and amounts of components and ingredients. For example, deodorant compositions which contain less than the minimum concentration of components of 45% are unlikely to result in a deodorant composition having a deodorant value of at least 0.50. Therefore, in preparing the best deodorant compositions of the invention, the rules for selection of components according to their classification, the representation of different classes, the amounts of each component present, bearing in mind the threshold value below which it is believed a component will not significantly contribute, are all important to observe if the best results are to be obtained.

It should be explained that components present in the deodorant product for purposes other than obtaining deodorant effects, for example an adjunct like the antioxidant included for the stabilisation of the product, are excluded from the operation of the preceding instructions to the extent that the component is required for that other purpose. The levels at which adjuncts are conventionally present is well-established for established materials and readily determinable for new materials so that the application of the above exclusion presents no difficulty.

Deodorant compositions can be incorporated in deodorant products according to the invention, at a concentration of from about 0.1 to about 20%, preferably from 0.5 to 10% and most preferably from 1 to 5% by weight.

It is apparent that if less than 0.1% of a deodorant composition is employed, then use of the deodorant product is unlikely to provide a significant reduction in malodour intensity. If more than 20% of a deodorant composition is employed, then use of the deodorant product is unlikely to further reduce malodour intensity beyond that observed at the 20% level.

2. THE CARRIER

The carrier for the deodorant composition can function as a diluent, dispersant, a substrate or other means for conveying and/or distributing the deodorant composition in the environment where a deodorising effect is required.

The carrier can also perform other functions such as cleansing, bleaching and polishing which characterise the function of the product other than that of acting as a deodorant.

When the carrier comprises an abrasive material it is generally a water-insoluble particulate abrasive material in which the particle size diameters are usually from 1 to 250 microns, the material usually having a specific gravity of from 0.5 to 5, and a Mohs' hardness of 2 to 7. Preferably, the diameter of the particles is from 10 to 150, most preferably from 20 to 100 microns. The specific gravity of the material is preferably from 1 to 3.

Examples of suitable abrasive materials include, but are not limited to, quartz, pumice, pumicite, titanium dioxide, silica sand, calcium carbonate, zirconium silicate, diatomaceous earth, whiting, felspar, alumina, corundum, volcanic ash, bentonite, magnesium oxide, magnesium carbonate, chalk, dolomite, shell, talc, calcite and mixtures thereof.

The amount of abrasive material when present in the deodorant product will normally be that which is appropriate for the normal function of the product other than that of a deodorant. The deodorant product can therefore in general terms contain up to 99% by weight of abrasive material. If, for example, the product is dry abrasive cleaner, the amount of abrasive material present will preferably be from 60 to 99% by weight of the product. If, however, the product is a liquid abrasive cleaner, then the amount of abrasive material present will normally be from 1 to 60% by weight of the product.

When the carrier comprises a bleaching agent, the bleaching agent will normally be one which is a hypochlorite or a hypobromite, or in the case of a dry product, a precursor thereof. Those bleaching agents which yield a hypochlorite species in aqueous solution and are therefore suitable for use in liquid products include alkali earth metal hypochlorites, hypochlorite addition products, chloramines, chlorimines, chloramides, and chlorimides. Specific examples of compounds of this type include sodium hypochlorite, potassium hypochlorite, monobasic calcium hypochlorite, dibasic magnesium hypochlorite, chlorinated trisodium phosphate dodecahydrate, potassium dichloroisocyanurate, sodium dichloroisocyanurate, 1,3-dichloro-5,5-dimethylhydantoin, and N-chlorosulphamide and mixtures thereof. A preferred agent is sodium hypochlorite.

Those bleaching agents which are suitable for use in powdered products and which are capable of liberating a hypohalite when the powdered product is employed in contact with water, for example in the cleaning of household industrial surfaces, are exemplified by heterocyclic N-bromo and N-chloro imides such as trichlorocyanuric tribromocyanuric acid, dibromocyanuric acid and dichlorocyanuric acid, and salts thereof with water-solubilising cations such as potassium and sodium. Other N-bromo and N-chloro imides may be used, such as N-brominated and N-chlorinated succinimide, malonimide, phthalimide and naphthalimide. Other suitable bleaching agents are the hydantoins, such as 1,3-dibromo- and 1,3-dichloro-5,5-dimethylhydantoin; N-monochloro-C,C-dimethylhydantoin methylene-bis, (N-bromo-C,C-di-methylhydantoin); 1,3-dibromo- and 1,3-dichloro-5-isobutylhydantoin; 1,3-bromo- and 1,3-dichloro-5-methyl-5-ethylhydantoin; 1,3-dibromo- and 1,3-dichloro-5,5-diisobutyl-hydantoin; and 1,3-dibromo- and 1,3-dichloro-5-methyl-5-amyl-hydantoin. Other useful bleaching agents are tribromomelamine and trichloromelamine. Dry, particulate, water soluble anhydrous inorganic salts are likewise suitable, such as lithium hypochlorite and lithium hypobromite. The bleaching agents may, if desired, be provided in the form of a stable, solid complex or hydrate, such as sodium p-toluene-sulphobromamine-trihydrate, sodium benzene-sulpho-chloraminedihydrate or calcium hypobromite tetrahydrate calcium hypochlorite tetrahydrate. Brominated and chlorinated trisodium phosphate formed by the reaction of the corresponding sodium hypohalite solution with trisodium phosphate (and water as necessary) also are efficaceous materials. Use may be made of bleaching agents capable of liberating hypochlorite as well as hypobromite such as N-brominated, N'-chlorinated heterocylic imides, for example N-bromo, N'-chlorocyanuric acids and salts thereof, e.g. N-monobromo-N,N-dichlorocyanuric acid, N-monobromo-N-monochlorocyanuric acid, N-monobromo-N-monochlorocyanuric acid, sodium-N-monobromo-N-monochlorocyanurate, potassium-N-monobromo-N-monochlorocyanurate; and N-brominated, N-chlorinated hydantoins, e.g. N-bromo-N-chloro-5,5-dimethyl-hydantoin and N-bromo-N-chloro-5-ethyl-5-methyl hydantoin.

The amount of bleaching agent when present in the deodorant product will normally be that which is appropriate for the normal function of the product other than that of a deodorant. The deodorant product can therefore contain up to 50%, preferably from 0.1 to 25%, most preferably from 0.5 to 10% by weight of the product of a bleaching agent, the chosen amount depending on the nature and function of the product.

When the carrier comprises a wax, the wax can be any natural, synthetic wax or waxy substance that can find utiliy in polishes.

Examples of natural waxes are vegetable waxes such as carnauba wax, cauassu wax, candelilla wax, ouricuri wax, raffia wax, palm wax, esparto wax, sugar cane wax, and cotton wax; animal waxes such as beeswax, ghedda wax, chinese insect wax, shellac wax, lanolin and walrat (spermaceti); mineral waxes such as paraffin wax, microcrystalline waxes, ozokerite-ceresin, petroleum waxes, montan wax.

Examples of synthetic waxes are fatty alcohols such as lanette wax; fatty acid esters of polyhydric alcohols such as glyceryl distearate, glyceryl monostearate, ethylene glycol monostearate, diethylene glycol monostearate; chlorinated products such as chlorinated naphthalene waxes, chlorinated paraffin waxes; synthetic waxes containing nitrogen such as Acrawaxes (Glycol Products Co), Armowax (Armour Co.); pseudoester waxes such as alkylamide waxes, ester-pseudoester waxes, arylamide waxes; silicone waxes; and polyethylene waxes, polypropylene glycol waxes and polyethylene glycol waxes such as carbowaxes.

The amount of wax when present in the deodorant product will normally be that which is appropriate for the normal function of the product other than that of a deodorant. The deodorant product can therefore contain up to 99.9%, preferably from 1 to 80% by weight of the product of a wax, the chosen amount depending on the nature and function of the product.

When the carrier comprises a film forming polymer, it is usually one which has the property of forming a hard, glossy, durable film on a surface such as a floor which is likely to suffer wear and tear from passage thereover of people, animals, furniture and equipment. Examples of suitable polymers are those which can be formed from polymerisable ethylenically unsaturated monomers such as styrene, lower alkyl methacrylates in which the alkyl group contains from 1 to 12 carbon atoms, lower alkyl acrylates in which the alkyl group contains from 1 to 12 carbon atoms, acrylonitrile and/or methacrylonitrile. An example of a styrene polymer is polystyrene. Specific examples of alkyl methacrylates include methyl, ethyl, propyl, isopropyl, butyl, pentyl, hexyl, heptyl, octyl, nonyl, decyl, undecyl, dodecyl, 2-ethyl hexyl, and cyclohexyl methacrylates. Suitable alkyl acrylates include methyl, ethyl, propyl, butyl, pentyl, hexyl, heptyl, octyl, nonyl, decyl, undecyl, dodecyl, 2-ethyl hexyl, and cyclohexyl acrylates, the polymer should contain no more than about 30% butyl or higher alkyl acrylates, since these acrylates soften the polymer more than the short chain alkyl acrylates.

Further examples of film forming polymers include nonvolatile silicone fluids and 'waxes' such as polyalkylsiloxanes, for example polydimethylsiloxane; polyalkylarylsiloxanes, for example polymethylphenylsiloxane; polyethersiloxane copolymers, for example dimethylpolyoxyalkylene ether copolymer; and poly higher alkylpolysiloxanes, where the alkyl group has 3 or more carbon atoms.

Further examples of suitable film forming polymers include graft polymers of low molecular weight styrene-maleic anhydride resins with heterocyclic compounds such as ε-caprolactam, 2-pyrrolidone or N-methyl-2-pyrrolidone, as well as the water-soluble alkali metal or ammonium salts of these graft polymers.

Yet further examples of film forming polymers include copolymers such as polystyrene, ethyl acrylate-acrylic acid copolymers, styrene-acrylate copolymers, ethyl acrylate-methacrylate acid copolymers, rosin acrylate copolymers and organic polycarboxylic acid copolymers.

Other suitable film forming polymers include resins such as zinc resinate, and white glyptal resin.

It is also possible to employ two or more film forming polymers in the deodorant product of the invention.

The amount of film forming polymer when present in the deodorant product does not normally exceed 50% by weight of the product. Preferably, the amount of film forming polymer forms from 0.1 to 25%, most preferably from 0.5 to 15% by weight of the product.

It is to be understood that the foregoing carriers are merely illustrative of the carriers which are suitable for incorporation in the products of the invention.

In general terms it can be stated that the carrier will form from 0.1 to 99.9%, usually from 1 to 99% by weight of the product. The preferred amount of carrier to be employed will, as can be seen from the foregoing discussion, be dictated by the category of carrier employed and the physical nature of the end product.

3. PRODUCTS OF THE INVENTION

The deodorant product of the invention can take many forms, depending upon whether it is intended for use in a domestic, commercial, industrial or agricultural environment, where human contact is likely to occur and where maladours are accordingly likely to be perceived.

Products of the invention can then be classified according to their ultimate utility, but it is to be understood that the invention is not limited solely to these examples.

According to the following classification, the compositions of the invention can take the form of solid products or liquid products which contain a deodorising amount of the deodorant composition.

Examples of products of the invention which are domestic, commercial, industrial or agricultural products for use other than for direct application to the human body are abrasive cleaners, bleach products, paints and polishes intended for application to surfaces in an environment where malodour can exist or develop.

It is to be understood that products of the invention will normally contain further ingredients in addition to the deodorant composition and the carrier, as herein defined, appropriate to their normal function, for example as cleaners or polishes, these further ingredients being those conventionally employed in such products.

Products of the invention will usually be packed in a container suited to their ultimate use when dispensing and deploying the product in order to prevent or reduce the development of malodour. The construction and design of the container will also usually be dictated by the physical form of the product.

Containers suitable for containing and, when required, dispensing powdered products such as powder abrasive cleaners can be cannisters of board, metal or plastics material, perforated at one end to allow the powdered product to be sifted onto a surface. Similarly, containers for liquid products can be glass or plastic bottles or cannisters which can be uncapped or perforated when required for use. Liquid products can also be packed in cannisters fitted with a suitable pump spray for dispensing by finger or hand pressure, or when the product comprises a propellant liquid or gas, pressurised dispensers such as aerosol devices are suitable containers.

Other containers for household, domestic, industrial or agricultural powdered or liquid products as are conventionally employed, can be used to contain and dispense products of the invention.

4. PROCESS FOR PREPARING DEODORANT PRODUCTS

The invention also provides a process for preparing deodorant products as herein defined.

Deodorant products of the invention can accordingly be prepared by mixing or blending the deodorant composition with one or more carriers. Where a heat treatment is employed in preparing the deodorant products, it is preferable to add the deodorant composition to the carrier and other ingredients of the product towards the end of the process when loss of any volatile substances in the deodorant composition is minimised.

5. METHOD OF SUPPRESSING MALODOUR

The invention also provides a method for suppressing malodour.

Products of the invention can accordingly be deployed in an effective amount in an environment where malodour exists or is likely to develop. For example, products of the invention such as abrasive cleaners, bleaches and polishes can be applied to kitchen, bathroom and other surfaces including floors, sinks, baths or lavatory basins and bowls in order to clean, bleach or polish these surfaces, while at the same time providing a deodorising effect which can be long lasting.

6. EXAMPLES OF PRODUCTS OF THE INVENTION

The following products are illustrative of compositions of the invention which comprise a carrier, which can be a liquid or a solid carrier, onto or into which a deodorant composition can be incorporated, included or deposited.

In the following examples, the proportion of ingredients are in parts by weight.

| Scouring powder for kitchen and household use | |
|---|---|
| Hard soap, powdered | 70 |
| Sodium metabisulphite | 50 |
| Sodium carbonate | 80 |
| Trisodium phosphate | 50 |
| Chalk | 749 |
| Deodorant composition | 1 |
| Bath Cleaner | |
| Trisodium phosphate | 250 |
| Soap, powdered | 250 |
| Chalk | 499 |
| Deodorant composition | 1 |
| Lavatory Cleaner | |
| Sodium hydrogen sulphate | 600 |
| Alum (powdered) | 300 |
| Salt | 98 |
| Deodorant composition | 2 |
| Laundry Bleach | |
| Calcium hypochlorite | 500 |
| Monocalcium phosphate | 498 |
| Deodorant composition | 2 |
| Floor Polish | |
| Carnauba wax | 150 |
| Cumarone resin | 60 |
| Oleic acid | 40 |
| Triethanolamine | 40 |
| Borax | 60 |
| Water | 245 |
| Deodorant composition | 5 |
| Antiseptic Insecticidal Floor and Furniture Polish | |
| Terpentine | 645 |
| Terpineol | 50 |
| Derris, powdered | 30 |
| Pyrethrum, powdered | 30 |
| Bornyl acetate | 20 |
| Bornyl chloride | 20 |
| Zinc resinate | 5 |
| Deodorant composition | 5 |
| Window Polish | |
| Diglycol stearate | 150 |
| Water | 495 |
| Magnesium carbonate | 150 |
| Chalk | 100 |
| White bole | 100 |
| Deodorant composition | 5 |
| Furniture Polish | |
| Beeswax | 25 |
| Diglycol stearate | 10 |
| Montan wax | 25 |
| Rosin | 3 |
| Ozokerite (60/62° C.) | 17 |
| Ammonia | 70 |
| Water | 848 |
| Deodorant composition | 2 |
| White Gloss Enamel Paint | |
| Stock ½ second pyroxylin | 400 |
| White glyptal resin (film-forming polymer) | 180 |
| Thinners | 380 |
| Plasticiser | 70 |
| Cellosolve | 60 |
| Pigment (white) | 340 |
| Deodorant composition | 20 |

7. SPECIFIC EXAMPLES OF THE INVENTION ILLUSTRATING DEODORANT EFFECTIVENESS

The invention is illustrated by the following examples, in which all parts and percentages are by weight.

In each of Examples 1 to 6 a deodorant composition was prepared by mixing the components and other ingredients listed in the relevant Deodorant Composition, which gives the amount of components in each class. Test products containing the deodorant composition and control products containing no deodorant composition were prepared and tested in each instance.

EXAMPLE 1

This Example illustrates the invention in terms of a polish suitable for application to floors to provide a hard, clear, shiny non-slip protective coating.

The test polish contained the following ingredients:

|  | % w/w |
|---|---|
| Polyethylene wax (AC 629) (a) | 2.4 |
| Copolymer (PRIMAL B231) (b) | 12.8 |
| Resin (SR 88) (c) | 0.8 |
| Synperonic A7 (d) | 0.9 |
| 2-amino-2-methyl propanol | 0.18 |
| Oleic acid | 0.3 |
| Tributoxyl ethyl phosphate | 0.6 |
| PROXEL AB paste (e) | 0.03 |
| FC 128 (f) | 0.006 |
| Carbitol | 1.6 |
| Industrial methylated spirit | 0.8 |
| Ammonia | 0.27 |
| Deodorant Composition 1 | 0.2 |
| Water to | 100 |

(a) A wax manufactured by Allied Chemicals having a softening point of 101° C., a specific gravity of 0.93 and an acid value of 14 to 17.
(b) Styrene acrylate copolymer manufactured by Rohm & Haas.
(c) Rosin maleic anhydride manufactured by Schenectady Chemicals Inc., and having a melting point of 150 to 160° C., and an acid value of 185 to 200.
(d) A synthetic primary alcohol ethylene oxide condensate (nonionic detergent) manufactured by ICI and having an HLB value of 12.2.
(e) A preservative manufactured by ICI.
(f) 1% solution of the potassium salt of N—ethyl-N—perfluoro octane sulphonyl glycine manufactured by 3M Company.

The formulation of the Deodorant Composition 1 is as follows:

| Deodorant Composition 1 | Parts | Class | Total in class |
|---|---|---|---|
| Components | | | |
| iso-Amyl salicylate | 5.0 | 1 | |
| Benzyl salicylate | 4.0 | 1 | 10.25 |
| LRG 201 | 1.25 | 1 | |
| Bergamot AB 430 | 15.0 | 2 | |
| Geranium AB 76 | 4.0 | 2 | 20.7 |
| Opoponax resinoid | 1.7 | 2 | |
| 1,3,4,6,7,8-Hexahydro-4,6,6,-7,8,8-hexamethylcyclopenta-α-2-benzopyran | 10.0 | 4 | 10.0 |
| o-t-Butylcyclohexyl acetate | 0.5 | 5 | |
| Diethyl phthalate | 3.75 | 5 | 4.25 |
| Nonanolide-1,4 | 0.2* | (5) | |
| Ingredients | | | |
| Amber AB 358 | 3.0 | | |
| Benzyl alcohol | 0.15 | | |
| Cedar atlas oil | 5.0 | | |
| Citronellol | 7.0 | | |
| Citronella oil | 16.1 | | |
| Citronellyloxyacetaldehyde | 0.5 | | |
| Hexyl aldone | 0.7 | | |
| Jasmin AB 284 | 12.0 | | |
| Orange oil sweet | 8.0 | | |

-continued

| Deodorant Composition 1 | Parts | Class | Total in class |
|---|---|---|---|
| 10-Undecen-1-al | 0.15 | | |
| Vetyvert oil | 2.0 | | |
|  | 100.0 | | |
| Total amount of components | | | 45.2 |
| Number of components present | | | 9 |
| Average amount of each component | | | 5.0 |
| Number of classes represented | | | 4 |

*eliminated from calculation - below threshold value of 0.5%.

The deodorant value of Deodorant Composition 1 was determined by the Deodorant Value test as described hereinbefore and was calculated as the difference between the control and test soap bar series. The results were as follows:

| Deodorant value of Deodorant Composition 1 | Control soap bar | Test soap bar |
|---|---|---|
| Average scores | 3.46 | 2.93 |
| Deodorant value (difference) | | 0.53 |

A control polish was also prepared which was identical except that the Deodorant Composition 1 was omitted.

The ability of the test polish compared with that of the control polish to reduce malodour was assessed as follows:

Each polish was painted onto the outside of glass vials of surface area 25 cm² and allowed to dry for 1 hour. The amount of polish applied was such that the residual dried film on each vial weighed 0.01 g. A polish coated vial was then placed in a series of air tight screw capped jars together with 5 ml of each of four different concentrations of a standard kitchen malodour prepared according to the table below. One hour later, each jar was uncapped and the odour within assessed according to a 0 to 5 hedonic scale by a panel of trained assessors.

The standard kitchen malodour concentrate was prepared from the following ingredients:

| Kitchen malodour concentrate: GSA-FSS P-D-00200a* | % w/w |
|---|---|
| diacetyl (2,3-butanedione) | 3.85 |
| Pyridine | 3.85 |
| diallyl sulphide (thio-allyl ether) | 9.23 |
| dimethyl sulphide | 40.00 |
| Heptaldehyde | 3.85 |
| Paraldehyde | 1.90 |
| Propionic acid | 36.92 |
| Glacial acetic acid | 0.40 |

*General Services Administration Federal Supply Service Interim Federal Specification The kitchen malodour concentrate was then diluted with odourless paraffin oil according to the following table to provide a basis for the odour scores recorded.

| Concentration g kitchen odour per 1 paraffin oil | Odour score |
|---|---|
| 0.004 | 1 |
| 0.01 | 2 |
| 0.056 | 3 |

| | Concentration g kitchen odour per 1 paraffin oil | Odour score |
|---|---|---|
| | 0.32 | 4 |

The particular dilutions of kitchen malodour chosen corresponded, so far as odour level was concerned, with the standard solutions 1 to 4 of isovaleric acid referred to in the Deodorant Value Test which were used for reference purposes by the panel of trained assessors in the evaluation of axilliary body malodour as described in that Test. The assessors were accordingly able to assess with remarkable consistency the malodour level in the screw topped jars employed in the malodour reduction tests described in Example 1 and the remaining Examples.

The results which were analysed statistically in each case and for Example 1 can be summarised as follows:

| | Malodour reduction value of polish | |
|---|---|---|
| | Control polish | Test polish |
| Average scores | 3.63 | 1.42 |
| Malodour reduction value of test polish | | 2.21 |

This result indicated that the test polish possessed a substantial capacity for reducing malodour.

It should be understood that the 'Deodorant Value' of the deodorant composition and the 'Malodour Reduction Value' of the corresponding product recorded in Example 1 cannot be compared numerically with each other, as the criteria involved in each test were different. The same consideration applies to the remaining Examples.

EXAMPLE 2

This example illustrates the invention in terms of a bleach product suitable for application to sinks, baths and ceramic sanitary were to provide a cleaning, bleaching and deodorising action.

The test bleach product contained the following ingredients:

| | % w/w |
|---|---|
| Caustic soda (47%) | 1.15 |
| Lauric acid | 0.9 |
| Sodium stearate | 0.61 |
| EMPIGEN OB (30%) (a) | 5.48 |
| STS (40%) (b) | 1.88 |
| Sodium silicate (47%) (c) | 0.11 |
| UMB (d) | 0.03 |
| Sodium hypochlorite 15% | 40 |
| Calcium chloride | 0.16 |
| Deodorant Composition 2 | 0.2 |
| Water to | 100 |

(a) lauryl dimethyl amine oxide
(b) sodium toluene sulphonate
(c) 2:1 $SiO_2:Na_2O$
(d) ultramarine blue pigment The formulation of Deodorant Composition 2 was as follows:

| Deodorant Composition 2 | | | |
|---|---|---|---|
| Components | Parts | Class | Total in class |
| Carvacrol | 3.5 | 1 | 4.5 |
| Thyme oil red | 1.0 | 1 | |
| Bergamot AB 37 | 20.0 | 2 | 30.0 |
| Pomeransol AB 413 | 6.0 | 2 | |
| Petitgrain oil | 4.0 | 2 | |
| 6-Acetyl-1,1,3,4,4,6-hexa-methyl-tetrahydro-naphthalene | 3.0 | 3 | 8.0 |
| β-Methyl naphthyl ketone | 5.0 | 3 | |
| 3a-Methyl-dodecahydro-6,6,9a-trimethyl naphtho-2(2,1-b) furan | 0.25* | (4) | |
| β-Naphthyl methyl ether | 9.0 | 4 | 9.0 |
| Ingredients | | | |
| Citronellyl acetate | 5.0 | | |
| Dipropylene glycol | 4.75 | | |
| Geranyl nitrile | 1.5 | | |
| Indole | 1.0 | | |
| Lemongrass oil | 3.0 | | |
| Lime AB 402 | 10.0 | | |
| Lavendin oil | 4.0 | | |
| l-Menthol | 8.0 | | |
| Neroli AB 78 | 6.0 | | |
| Orange oil sweet | 5.0 | | |
| | 100.0 | | |
| Total amount of components | | | 51.5 |
| Number of components present | | | 8 |
| Average amount of each component | | | 6.4 |
| Number of classes represented | | | 4 |

*eliminated from calculation - below threshold value of 0.5%.

The deodorant value of Deodorant Composition 2 was determined by the Deodorant Value Test as described herein before with the following results:

| Deodorant Value of Deodorant Composition 2 | | |
|---|---|---|
| | Control soap bar | Test soap bar |
| Average scores | 3.34 | 2.73 |
| Deodorant value (difference) | | 0.61 |

A control bleach product was also prepared which was identical except that the Deodorant Composition 2 was omitted.

The ability of the test bleach compared with that of the control bleach product to reduce malodour was assessed generally according to the method described in Example 1, but with the following differences.

The bleach was poured into a 10 ml capacity glass vial and the following procedure was adopted:
(i) fill vial with bleach to maximum volume of 10 ml,
(ii) immediately empty vial by inverting it and allowing to drain for 30 minutes,
(iii) almost fill with water and shake,
(iv) empty vial again and drain,
(v) wipe interior of vial with paper tissues and leave for 1 hour.

Glass vials which had been treated in this manner with either test or control bleach product were then placed in a series of screw top glass jars together with the graded series of standard kitchen malodours as described in Example 1. Malodour reduction values were assessed as previously described.

The statistically analysed results were as follows:

| Malodour reduction value of bleach | | |
| --- | --- | --- |
| | Control bleach | Test bleach |
| Average score | 2.54 | 1.25 |
| Malodour reduction value of test bleach | | 1.29 |

This result indicated that the test bleach very effectively reduced malodour.

EXAMPLE 3

This example illustrates the invention in terms of a strippable polish suitable for application to furniture.

The test polish contained the following ingredients:

| | % w/w |
| --- | --- |
| Wax emulsion (a) | 75.6 |
| Alkaline soluble resin solution (b) | 16.0 |
| Tributoxyethyl phosphate (c) | 0.4 |
| Levelling aid (d) | 0.5 |
| Anionic surfactant solution (e) | 3.0 |
| Deodorant Composition 3 | 0.2 |
| Ammonia (to adjust to pH 10.4) | |
| Water to | 100 |

(a) the wax emulsion had the following formulation:
Montan Wax KFO (Hoechst) 12
Diethyl amino-ethanol 2.24
Water to 100
(b) LYTRON 812, a 10% aqueous emulsion of a styrene-maleic anhydride copolymer (Monsanto)
(c) KP 140 (Albright & Wilson)
(d) FC 128, a 1% solution of the potassium salt of N—ethyl-N—perfluoro-octane sulphonyl glycine (3M Co.)
(e) TERGITOL 7, a 27% aqueous solution of a sulphonated derivative of 3,9-diethyl-6-trideconol (Union Carbide)

The formulation of Deodorant Composition 3 was as follows:

| Deodorant Composition 3 | | | |
| --- | --- | --- | --- |
| | Parts | Class | Total in class |
| Components | | | |
| Mousse de chene Yugo | 1.25 | 1 | 11.25 |
| Pimento leaf oil | 10.0 | 1 | |
| Benzoin Siam resinoid | 5.0 | 2 | |
| Bergamot AB 430 | 15.0 | 2 | 25.0 |
| Geranium oil | 5.0 | 2 | |
| p-t-Amylcyclohexanone | 5.0 | 3 | 17.0 |
| α-iso-Methyl ionone | 12.0 | 3 | |
| Coumarin | 4.0 | 4 | |
| 1,3,4,6,7,8-Hexahydro-4,6,6,7,8,8-hexamethyl-cyclopenta-α-2-benzopyran | 3.0 | 4 | 7.0 |
| Diethyl phthalate | 4.35 | 5 | 4.35 |
| Ingredients | | | |
| Hercolyn D | 12.25 | | |
| Lavendin oil | 10.0 | | |
| Musk ambrette | 3.0 | | |
| Rosenta AB 380 | 10.0 | | |
| Rose-D-oxide | 0.15 | | |
| | 100.0 | | |
| Total amount of components | | | 64.6 |
| Number of components present | | | 10 |
| Average amount of each component | | | 6.5 |
| Number of classes represented | | | 5 |

The deodorant value of Deodorant Composition 3 was determined by the Deodorant Value test as described hereinbefore with the following results:

| Deodorant Value of Deodorant Composition 3 | | |
| --- | --- | --- |
| | Control soap bar | Test soap bar |
| Average scores | 3.04 | 2.47 |
| Deodorant value (difference) | | 0.57 |

A control polish was also prepared which was identical except that the Deodorant Composition 3 was omitted.

The ability of the test polish compared with that of the control polish to reduce malodour was assessed generally as described in Example 1.

The statistically analysed results were as follows:

| Malodour reduction value of polish | | |
| --- | --- | --- |
| | Control polish | Test polish |
| Average scores | 3.46 | 1.96 |
| Malodour reduction value of test polish | | 1.50 |

This result indicated that the test polish possessed a considerable ability to reduce malodour.

EXAMPLE 4

This example illustrates the invention in terms of a bleach product suitable for application to sinks, baths and ceramic sanitary ware to provide cleaning, bleaching and deodorising action.

The test bleach product contained the following ingredients:

| | % w/w |
| --- | --- |
| Sodium hypochlorite (15% solution) | 66.6 |
| Amine oxide (30%) (a) | 2.5 |
| Lauric acid | 0.23 |
| Sodium hydroxide | 1.00 |
| Deodorant Composition 4 | 0.1 |
| Water to | 100 |

(a) lauryl dimethylamine oxide

The formulation of Deodorant Composition 4 was as follows:

| Deodorant Composition 4 | | | |
| --- | --- | --- | --- |
| | Parts | Class | Total in class |
| Components | | | |
| Ethyl vanillin | 0.2* | (1) | |
| iso-Eugenol | 5.0 | 1 | 6.25 |
| LRG 201 | 1.25 | 1 | |
| Bergamot AB 430 | 8.0 | 2 | 15.0 |
| Patchouli oil | 7.0 | 2 | |
| 2-n-Heptylcyclopentanone | 0.5 | 3 | 5.5 |
| α-iso-Methyl ionone | 5.0 | 3 | |
| β-Naphthyl methylether | 7.5 | 4 | 7.5 |
| p-t-Butylcyclohexyl acetate | 4.3 | 5 | |
| Diethyl phthalate | 8.25 | 5 | |
| i-Nonyl formate | 5.0 | 5 | 26.55 |
| Nonanediol-1,3-diacetate | 4.0 | 5 | |
| Phenylethyl phenyl acetate | 5.0 | 5 | |
| Tetrahydro muguol | 6.0 | 6 | 6.0 |
| Ingredients | | | |
| Citronella oil | 6.0 | | |
| Green Herbal AB 502 | 15.0 | | |
| Indole | 1.5 | | |
| Rosenta AB 380 | 6.0 | | |

-continued

| Deodorant Composition 4 | | | |
|---|---|---|---|
| | Parts | Class | Total in class |
| Sandalone | 4.0 | | |
| α-Undecalactone | 0.5 | | |
| | 100.0 | | |
| Total amount of components | | | 66.8 |
| Number of components present | | | 14 |
| Average amount of each component | | | 4.8 |
| Number of classes represented | | | 6 |

*eliminated from calculation - below threshold value of 0.5%.

The deodorant value of Deodorant Composition 4 was determined by the Deodorant Value Test as described hereinbefore with the following results:

| Deodorant Value of Deodorant Composition 4 | | |
|---|---|---|
| | Control soap bar | Test soap bar |
| Average scores | 3.25 | 2.10 |
| Deodorant value (difference) | | 1.15 |

A control bleach product was also prepared which was identical except that the deodorant composition was omitted.

The ability of the test bleach compared with that of the control bleach product to reduce malodour was assessed generally according to the method described in Example 2.

The statistically analysed results were as follows:

| Malodour reduction value of bleach | | |
|---|---|---|
| | Control bleach | Test bleach |
| Average values | 2.46 | 1.42 |
| Malodour reduction value of test bleach | | 1.04 |

This result indicated that the test bleach possessed a substantial ability to reduce malodour.

EXAMPLE 5

This example illustrates the invention in terms of a thickened liquid abrasive product suitable for cleaning sinks, baths and ceramic sanitary ware to provide both a cleaning and a deodorising action.

The test liquid abrasive product contained the following ingredients:

| | % w/w |
|---|---|
| $C_{10}$ to $C_{13}$ alkyl benzene sulphonate (DOBS 102) | 1.9 |
| Potassium soap of distilled groundnut oil | 0.6 |
| Coconut diethanolamide | 2.2 |
| Sodium tripolyphosphate | 5 |
| Calcite | 50 |
| Deodorant Composition 5 | 0.3 |
| Water to | 100 |

The formulation of Deodorant Composition 5 was as follows:

| Deodorant Composition 5 | | | |
|---|---|---|---|
| | Parts | Class | Total in class |
| Components | | | |
| Benzyl salicylate | 15.0 | 1 | } 21.0 |
| Mousse de chene Yugo | 6.0 | 1 | |
| Bergamot AB 430 | 15.0 | 2 | 15.0 |
| 6-Acetyl-1,3,3,4,4,6-hexamethyltetrahydronaphthalene | 2.5 | 3 | 2.5 |
| p-t-Amylcyclohexanone | 0.06* | (3) | |
| 3a-Methyl-dodecahydro-6,6,9a-trimethyl-naphtho-2(2,1-b) furan | 0.75 | 4 | 0.75 |
| Diethyl phthalate | 8.04 | 5 | 8.04 |
| Nonanolide-1,4 | 0.2* | (5) | |
| Dimyrcetol | 16.0 | 6 | 16.0 |
| Ingredients | | | |
| Cinnamic alcohol | 5.0 | | |
| Dimethyl benzyl carbinyl acetate | 2.5 | | |
| Dipropylene glycol | 14.25 | | |
| Geraniol | 5.0 | | |
| iso-Butyl phenyl acetate | 5.0 | | |
| Methyl salicylate | 0.5 | | |
| Pelargene | 4.0 | | |
| Trichloromethyl phenyl carbinyl acetate | 0.2 | | |
| | 100.0 | | |
| Total amount of components | | | 63.29 |
| Number of components present | | | 7 |
| Average amount of each component | | | 9.0 |
| Number of classes represented | | | 6 |

*eliminated from calculation - below threshold value of 0.5%.

The deodorant value of Deodorant Composition 5 was determined by the Deodorant Value Test as described hereinbefore with the following results:

| Deodorant Value of Deodorant Composition 5 | | |
|---|---|---|
| | Control soap bar | Test soap bar |
| Average scores | 3.30 | 2.70 |
| Deodorant value (difference) | | 0.60 |

A control liquid abrasive cleaner product was also prepared which was identical except that the Deodorant Composition 5 was omitted.

The ability of the test liquid abrasive cleaner compared with that of the control liquid abrasive cleaner to reduce malodour was assessed generally according to the method described in Example 2.

The statistically analysed results were as follows:

| Malodour reduction value of liquid abrasive cleaner | | |
|---|---|---|
| | Control cleaner | Test cleaner |
| Average scores | 3.14 | 2.25 |
| Malodour reduction value of test cleaner | | 0.89 |

The results indicated that the test liquid abrasive cleaner was capable of reducing malodour to a significant extent.

EXAMPLE 6

This example illustrates the invention in terms of a liquid abrasive floor cleaner product.

The test cleaner product contained the following ingredients:

| | % w/w |
|---|---|
| $C_{10}$ to $C_{13}$ alkyl benzene sulphonate (DOBS 102) | 3.4 |
| Potassium soap | 1.1 |
| Coconut diethanolamide | 4.0 |
| Sodium tripolyphosphate | 9.0 |
| Calcite | 10.0 |
| Deodorant Composition 6 | 0.3 |
| Water to | 100 |

The formulation of Deodorant Composition 6 was as follows:

| Deodorant Composition 6 | | | |
|---|---|---|---|
| | Parts | Class | Total in class |
| Components | | | |
| Clove leaf oil | 10.0 | 1 | 11.25 |
| LRG 201 | 1.25 | 1 | |
| Petitgrain oil | 10.0 | 2 | 10.0 |
| p-t-Butyl-α-methyl hydro cinnamic aldehyde | 15.0 | 3 | 15.0 |
| 3a-Methyl-dodecahydro-6,6,9a-trimethylnaphtho-2(2,1-b) furan | 0.5 | 4 | 0.5 |
| o-t-Butylcyclohexyl acetate | 2.0 | 5 | 21.25 |
| Diethyl phthalate | 9.25 | 5 | |
| i-Nonyl acetate | 10.0 | 5 | |
| Phenyl ethyl alcohol | 10.0 | 6 | 10.0 |
| Ingredients | | | |
| Benzyl propionate | 4.0 | | |
| Bergamot oil | 15.0 | | |
| Dimethyl benzyl carbinyl acetate | 5.0 | | |
| iso-Butyl benzoate | 5.0 | | |
| Neroli oil | 3.0 | | |
| | 100.0 | | |
| Total amount of components | | | 68.0 |
| Number of components present | | | 9 |
| Average amount of each component | | | 7.6 |
| Number of classes represented | | | 6 |

The deodorant value of the Deodorant Composition 6 was determined by the Deodorant Value Test as described hereinbefore with the following results:

| Deodorant Value of Deodorant Composition 6 | | |
|---|---|---|
| | Control soap bar | Test soap bar |
| Average scores | 3.25 | 2.33 |
| Deodorant value (differences) | | 0.92 |

A control liquid abrasive floor cleaner product was also prepared without the Deodorant Composition 6.

The ability of the test liquid abrasive cleaner compared with that of the control liquid abrasive cleaner to reduce malodour was assessed generally according to the method described in Example 2.

The statistically analysed results were as follows:

| Malodour reduction value of liquid abrasive floor cleaner | | |
|---|---|---|
| | Control floor cleaner | Test floor cleaner |
| Average scores | 2.89 | 2.00 |
| Malodour reduction value of test liquid floor cleaner | | 0.89 |

The results indicated that the test liquid abrasive cleaner was capable of reducing malodour to a significant extent.

EXAMPLE 7

This example illustrates the invention in terms of a powder abrasive surface cleaning product.

The test powder abrasive product contained the following ingredients:

| | % w/w |
|---|---|
| $C_{10}$ to $C_{16}$ alkyl benzene sulphonate flake (DOBS 055) (85% AD) | 3.0 |
| Trisodium orthophosphate | 3.0 |
| Deodorant Composition 5 | 0.3 |
| Felspar to | 100 |

A control powder abrasive product was also prepared without the Deodorant Composition 5.

The ability of the test powder abrasive product compared with that of the control powder abrasive product to reduce malodour was assessed in the following manner:

0.5 g powder was applied to a damp tissue and rubbed onto the outer surface of a glass vial (surface area 25 $cm^2$) and allowed to dry for 30 minutes. The outer surface of the vial was then wiped clean with a fresh damp tissue and the vial was allowed to stand at room temperature for a further 30 minutes. The vial was then placed in a screw top jar together with standard malodour as generally described in Example 1, sufficient vials being so prepared to provide replicates for both test and control abrasive powders and for each of the four malodour concentrations. One hour later, each jar was uncapped and the odour within assessed according to a hedonic scale by a panel of trained assessors.

The statistically analysed results were as follows:

| Malodour reduction value of powder abrasive surface cleaning product | | |
|---|---|---|
| | Control powder cleaner | Test powder cleaner |
| Average scores | 3.04 | 1.08 |
| Malodour reduction value of test powder cleaner | | 1.96 |

The results indicate that the test powder abrasive cleaner product was very effective in reducing malodour.

EXAMPLE 8

This example illustrates the invention in terms of a window polishing product.

The test polishing product contained the following ingredients:

| | % w/w |
|---|---|
| Phase A | |
| Silicone Fluid D C 200/50 cs (a) | 1.0 |
| EMULSOGEN MS 12 (b) | 1.5 |
| SHELLSOL T (c) | 12 |
| Phase B | |
| Deionised water to | 100 |
| Phase C | |
| Isopropyl alcohol | 20 |

| | % w/w |
|---|---|
| Deodorant Composition 2 | 0.4 |

(a) A siloxane manufactured by Dow Corning
(b) Oleyl polyglycolether manufactured by Farbwerke Hoechst AG
(c) A high boiling aliphatic hydrocarbon solvent manufactured by Shell Chemicals Limited.

The polishing product was prepared as follows:
Phase A was warmed to 70° to 75° C. and added to phase B at the same temperature with rapid stirring. Phase C warmed to 45° C. then added to the mixed phases A and B and cooled with slow stirring. A loose emulsion was obtained which needed stirring or shaking thoroughly before use.

A control polishing product was also prepared without Deodorant Composition 2.

The ability of the test polishing product compared with that of the control polishing product to reduce malodour was assessed generally according to the method described in Example 2.

The statistically analysed results were as follows:

| Malodour reduction value of window polishing product | | |
|---|---|---|
| | Control polishing product | Test polishing product |
| Average scores | 3.09 | 2.75 |
| Malodour reduction value of test polishing product (difference) | | 0.34 |

The results indicated that the test window polishing product possessed a marked ability to reduce malodour.

EXAMPLE 9

This example illustrates the invention in terms of an aerosol furniture polish.

The test aerosol furniture polish contained the following ingredients:

| | % w/w |
|---|---|
| Phase A | |
| MONTAN Wax (a) | 2.0 |
| Hoechst Wax KSS (b) | 2.0 |
| EMULSOGEN OG (c) | 1.5 |
| Phase B | |
| Silicone Fluid F111/300 (d) | 3.0 |
| SHELLSOL T (e) | 40.0 |
| Phase C | |
| Deionised water to | 100 |
| Preservative | q.s. |
| Phase D | |
| Deodorant Composition 3 | 0.3 |
| Aerosol Fill | |
| Concentrate | 82.0 |
| Hydrocarbon propellant (f) | 18.0 |

(a) HOESCHST WAX, an ester was manufactured by Farbwerke Hoechst AG.
(b) An ester wax based on MONTAN WAX
(c) Diglyceryl sesquioleate manufactured by Farbwerke Hoechst AG.
(d) A linear dimethyl polysiloxane (300 cs) at 25° C. manufactured by ICI.
(e) A high boiling, high flash aliphatic hydrocarbon (isoparaffins) solvent manufactured by Shell Chemicals.
(f) A blend of n-butane, n-propane and iso-butane having a pressure of 40 psig (2.812 kg/sq cm).

The aerosol furniture polish was prepared as follows:
Phase A was melted by heating it at 90° C. Phase B was heated to 80° C. and added to Phase A. Phase C was heated to 80° C. and added to the mixture of phases A and B with rapid stirring. The mixture was cooled rapidly with stirring to 20° C. Phase D was finally added with further stirring to provide the concentrate which was filled into aerosol cans together with the propellant mixture.

A control aerosol furniture polish was also prepared without the addition of phase C (Deodorant Composition 3).

The ability of the test aerosol furniture polish compared with that of the control furniture polish to reduce malodour was assessed in the following manner:

Smooth pieces of boxwood of surface area of 50 cm$^2$ were each sprayed for 1 second at a distance of 5 cm with either the test or control furniture polish and left to dry at room temperature for 10 minutes. Each boxwood piece was wiped with a clean cloth to remove surplus polish and then buffed lightly to obtain a shine.

The boxwood pieces were left at room temperature for a total of one hour after the initial spraying with polish and then each was placed in a series of screw top jars each containing 5 ml of one of the four concentrations of standard kitchen malodour. The jars were sealed and left for one hour and then the malodour in each jar was assessed according to the hedonic scale as previously described in Example 1.

The statistically analysed results were as follows:

| Malodour reduction value of aerosol furniture polish | | |
|---|---|---|
| | Control polish | Test polish |
| Average scores | 2.15 | 1.50 |
| Malodour reduction value of aerosol furniture polish (difference) | | 0.65 |

The results indicate that the test aerosol furniture polish was effective in reducing malodour.

APPENDIX

The following glossary provides further information, including the suppliers' names, which will aid identification of some of the aforementioned deodorant components and ingredients.

| | |
|---|---|
| Dimyrcetol | Dimyrcetol (IFF) |
| Hercolyn D | Tetrahydro abietate + dihydro abietate (HP) |
| LRG 201 | Oakmoss speciality (RB) |
| Pelargene | Pelargene (PPL) |
| Rose-D-Oxide | Rose oxide synthetic (PPL) |
| Sandalone | Sandalone (PPL) |
| Perfume Houses | |
| HP | Hercules Powder Co. |
| IFF | International Flavour & Fragrances Inc. |
| RB | Roure Bertrand |
| PPL | Proprietary Perfumes Ltd. |

All materials which are classified by a name and number, such as those having the 'AB' notation, are obtainable from Proprietary Perfumes Limited.

What is claimed is:
1. A deodorant product suitable for application to surfaces other than human skin, which product comprises:
   (i) from 1 to 99.9% by weight of a carrier selected from the group consisting of polishing agents and film forming polymers; and
   (ii) from 0.1 to 20% by weight of a deodorant composition comprising from 45 to 100% by weight of deodorant active components, said components have a lipoxidase-inhibiting capacity of at least 50% or a Raoult variance ratio of at least 1.1, said components being classified into six classes consisting of:
Class 1: phenolic substances
Class 2: essential oils, extracts, resins and synthetic oils
Class 3: aldehydes and ketones
Class 4: polycyclic compounds
Class 5: esters
Class 6: alcohols
provided that where a component can be classified into more than one class, it is placed in the lower or lowest numbered class; said components being so selected that
(a) the deodorant composition contains at least five components of which at least one must be selected from each of Class 1, Class 2 and Class 4;
(b) the deodorant composition contains components from at least 4 of the 6 classes; and
(c) any component present in the deodorant composition at a concentration of less than 0.5% by weight of said composition is eliminated from the requirements of (a) and (b);
the deodorant composition having a deodorant value of from 0.50 to 3.5 as measured by the Deodorant Value Test.

2. The deodorant product of claim 1, wherein the deodorant composition has a deodorant value of from 1.00 to 3.5 as measured by the Deodorant Value Test.

3. The deodorant product of claim 1, wherein the deodorant composition has a deodorant value of from 1.50 to 3.5 as measured by the Deodorant Value Test.

4. The deodorant product of claim 1, wherein the amount of deodorant components present in said class comprising phenolic substances and said class comprising essential oils, extracts, resins and synthetic oils and said class comprising polycyclic compounds, is at least 1% by weight of the deodorant composition for each of said classes and the amount of deodorant components present in said further class chosen from the remaining three classes is at least 1% by weight of the deodorant composition.

5. The deodorant product of claim 1, wherein the average concentration of all such components present is at least 5% by weight where four of said classes is represented, or at least 4.5% by weight where five or six of said classes is represented.

6. The deodorant product of claim 1, wherein the amount of deodorant components present in said class comprising phenolic substances and said class comprising essential oils, extracts, resins and synthetic oils and said class comprising polycylic compounds, is at least 3% by weight of the deodorant composition for each of said classes and the amount of deodorant components present in said further class chosen from the remaining three classes is at least 3% by weight of the deodorant composition.

7. The deodorant product of claim 1, wherein at least five of the classes is represented.

8. The deodorant product of claim 1, wherein all six classes are represented.

9. The deodorant product of claim 1, wherein the polishing agent is chosen from natural waxes and synthetic waxes.

10. The deodorant product of claim 1, wherein the said deodorant components are chosen from:
Class 1—Phenolic substances
  iso-Amyl salicylate
  Benzyl salicylate
  Carvacrol
  Clove leaf oil
  Ethyl vanillin
  iso-Eugenol
  LRG 201
  Mousse de chene Yugo
  Pimento leaf oil
  Thyme oil red
Class 2—Essential oils, extracts, resins, "synthetic" oils (denoted by "AB")
  Benzoin Siam resinoids
  Bergamot AB 37
  Bergamot AB 430
  Geranium AB 76
  Geranium oil
  Opoponax resinoid
  Patchouli oil
  Petitgrain oil
  Pomeransol AB 314
Class 3—Aldehydes and ketones
  6-Acetyl-1,1,3,4,4,6-hexamethyltetrahydronaphthalene
  p-t-Amyl cyclohexanone
  p-t-Butyl-$\alpha$-methyl hydrocinnamic aldehyde
  2-n-Heptylcyclopentanone
  $\alpha$-iso-Methyl ionone
  $\beta$-Methyl naphthyl ketone
Class 4—Polycyclic compounds
  Coumarin
  1,3,4,6,7,8-Hexahydro-4,6,6,7,8,9-hexamethyl cyclopenta-$\gamma$-2-benzopyran
  3a-Methyl-dodecahydro-6,6,9a-trimethylnaphtho-2-(2,1-b)furan
  $\beta$-Napthyl methyl ether
Class 5—Esters
  o-t-Butylcyclohexyl acetate
  p-t-Butylcyclohexyl acetate
  Diethyl phthalate
  Nonanediol-1,3-diacetate
  Nonanolide-1:4
  i-Nonyl acetate
  i-Nonyl formate
  Phenylethyl phenyl acetate
Class 6—Alcohols
  Dimyrcetol
  Phenylethyl alcohol
  Tetrahydromuguol 11. The deodorant product of claim 1 which is a floor polish comprising:
(i) from 1 to 80% by weight of a wax, and
(ii) from 0.5 to 10% by weight of a deodorant compositon, the deodorant active components of which comprise:
  iso-Amyl salicylate: (Class 1)
  Bergamot AB 430: (Class 2)
  1,3,4,6,7,8-Hexahydro-4,6,6,7,8,8-hexamethylcyclopenta-$\alpha$-2-benzopyran: (Class 4)
  Diethyl phthalate: (Class 5).

12. The deodorant product of claim 1 which is a furniture polish comprising:
(i) from 1 to 80% by weight of a wax, and
(ii) from 0.5 to 10% by weight of a deodorant composition, the deodorant active components of which comprise:
  Pimento leaf oil: (Class 1)
  Bergamot AB 430: (Class 2)

α-iso-Methyl ionone: (Class 3)

Coumarin: (Class 4).

13. The deodorant product of claim 1 which is a window polishing product comprising:
   (i) from 0.1 to 25% by weight of a film-forming polymer, and
   (ii) from 0.5 to 10% by weight of a deodorant composition, the deodorant active components of which comprise:
   Carvacrol: (Class 1).
   Bergamot AB 37: (Class 2)
   β-Methyl naphthyl ketone: (Class 3)
   β-Napthyl methyl ether: (Class 4).

14. The deodorant product of claim 1 which is a liquid polish, wherein the polishing agent forms from 1 to 25% by weight of the product.

15. The deodorant product of claim 1 which is a solid polish, wherein the polishing agent forms from 1 to 80% by weight of the product.

16. A method of suppressing malodor which comprises deploying an effective amount of the deodorant product of claim 1.

17. A process for preparing the deodorant product of claim 1, which comprises blending a deodorant composition with a carrier selected from the group consisting of polishing agents and film forming polymers, the deodorant composition having a deodorant value of from 0.50 to 3.5 as measured by the Deodorant Value Test.

* * * * *